United States Patent
Dzwonkiewicz

(10) Patent No.: US 6,454,704 B1
(45) Date of Patent: Sep. 24, 2002

(54) LIFTING CAP FOR A LARYNGOSCOPE

(75) Inventor: Mark R. Dzwonkiewicz, Crystal Lake, IL (US)

(73) Assignee: Mark Dzworkiewicz, Crystal Lake, IL (US)

(*) Notice: Subject to any disclaimer, the term of this patent is extended or adjusted under 35 U.S.C. 154(b) by 228 days.

(21) Appl. No.: 09/592,744

(22) Filed: Jun. 13, 2000

(51) Int. Cl.⁷ .............................................. A61B 1/267
(52) U.S. Cl. ........................ 600/185; 600/197; 600/226
(58) Field of Search .............................. 600/185, 197, 600/226

(56) References Cited

U.S. PATENT DOCUMENTS 5,065,738 A * 11/1991 Van Dam .................... 600/185
5,904,650 A * 5/1999 Wells ......................... 600/226
6,217,514 B1 * 4/2001 Gruen et al. ................. 600/185

* cited by examiner

Primary Examiner—Linda C. M. Dvorak
Assistant Examiner—Jocelyn Ram

(57) ABSTRACT

A lifting cap for a laryngoscope which facilitates oral endotracheal intubation. The lifting cap includes an abutment member, such as a plate, and fastener, such as a threaded shaft, which is adapted to attach the plate to the distal end of the handle of a laryngoscope. The plate extends radially outwardly from the handle a substantial distance to an outer peripheral edge. The lifting cap enables a user of the laryngoscope to abut their hand against the plate to provide a lifting force to the handle of the laryngoscope and to reduce the gripping pressure that would otherwise be required to be applied to the handle of the laryngoscope, while promoting proper lifting direction of the laryngoscope.

18 Claims, 1 Drawing Sheet

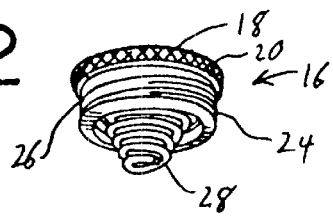
FIG. 2
PRIOR ART
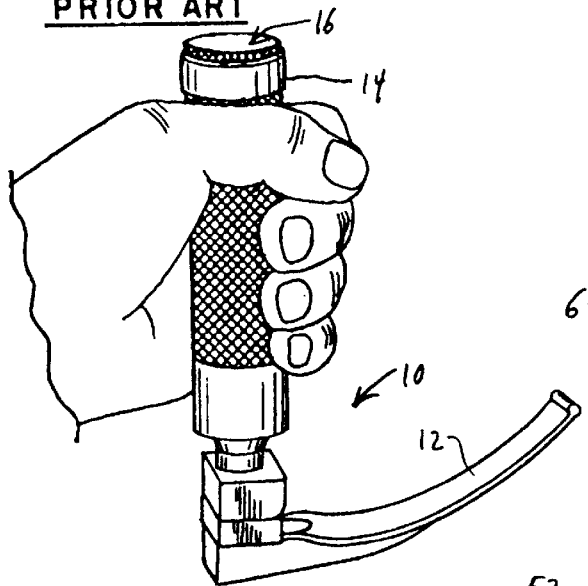
FIG. 1
PRIOR ART
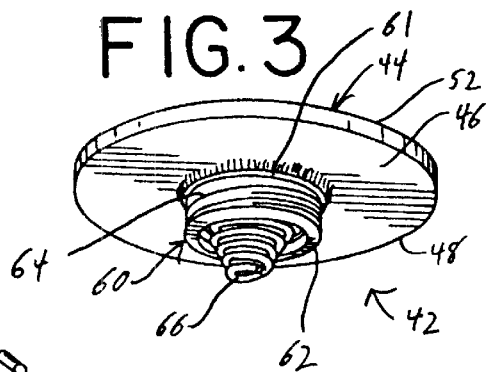
FIG. 3
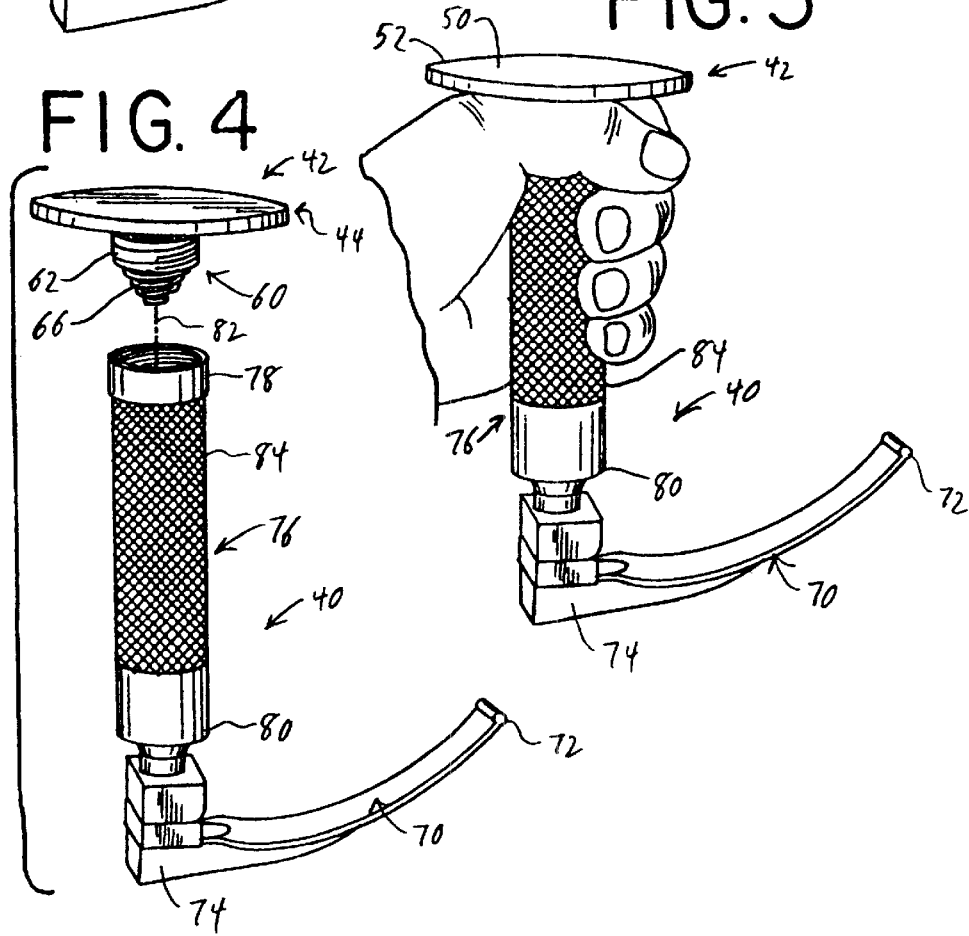
FIG. 5
FIG. 4

LIFTING CAP FOR A LARYNGOSCOPE

BACKGROUND OF THE INVENTION

The present invention is directed to a lifting cap adapted to be attached to the distal end of the handle of a laryngoscope to facilitate oral endotracheal intubation, and in particular to a lifting cap having an abutment member that is adapted to extend radially outwardly from the handle and a threaded shaft adapted to releasably connect the abutment member to the distal end of the handle.

In performing an oral endotracheal intubation procedure the blade of a laryngoscope is inserted into the mouth of a patient. The tip of the blade is positioned at or near the epiglottis depending on whether a straight or curved laryngoscope blade is being used. While the user manually grips the handle of the laryngoscope, the user lifts the laryngoscope along the central axis of the laryngoscope handle to lift the epiglottis and allow direct viewing of the vocal cords. In many cases, the lifting of the laryngoscope is difficult and two medical personnel may be required to achieve proper intubation. Lifting of the laryngoscope requires the user to maintain a strong manual grip on the laryngoscope handle to prevent the user's hand from slipping on the handle and often requires considerable force or strength to lift the laryngoscope in the proper direction. This often leads to undesired "cranking" or rotating of the laryngoscope which can cause trauma to the airway, broken or damaged teeth of the patient, and failed intubation attempts.

SUMMARY OF THE INVENTION

A lifting cap for a laryngoscope for use in facilitating oral endotracheal intubation. The laryngoscope includes a blade having a first end and second end wherein the first end is adapted to be inserted into the oral opening of a patient. The laryngoscope includes a handle adapted to be manually grasped by the hand of a user. The handle includes a first end, a second end, a central axis extending from the first end to the second end, and a peripheral surface extending around the central axis. The proximal or second end of the handle is coupled to the blade. The lifting cap is attached to the distal or first end of the handle. The lifting cap includes an abutment member such as a circular plate having a proximal surface that extends outwardly from adjacent the peripheral surface of the shaft to an outer edge. The lifting cap includes an end cap that is attached to the proximal surface of the plate. The end cap includes a threaded shaft that is adapted to be releasably attached to the first end of the handle. The lifting cap enables the user to loosen their grip on the handle and to slide their hand upward until it engages the proximal surface of the abutment member such that the user can apply force to the abutment member to lift the laryngoscope. The force applied by the user against the abutment member assists the user in lifting the handle in the proper direction while minimizing handle cranking.

BRIEF DESCRIPTION OF THE DRAWING FIGURES

FIG. 1 is a perspective view showing a prior art laryngoscope being manually grasped.

FIG. 2 is a perspective view of a prior art end cap of the laryngoscope shown in FIG. 1.

FIG. 3 is a perspective view of the lifting cap of the present invention.

FIG. 4 is an exploded view of a laryngoscope of the present invention including a lifting cap.

FIG. 5 is a perspective view of a laryngoscope having a lifting cap being grasped by a user.

DETAILED DESCRIPTION OF THE PREFERRED EMBODIMENTS

FIG. 1 shows a prior art laryngoscope 10 being manually grasped by the hand of a user. The prior art laryngoscope 10 includes a blade 12 that is attached to a generally cylindrical handle 14. The handle 14 is often tubular such that it may contain one or more batteries. The prior art laryngoscope 10 includes an end cap 16 as best shown in FIG. 2 that is removably attached to the distal end of the handle 14. The end cap 16 includes a generally circular end wall 18 having a circular peripheral edge 20. A tubular shaft 24 is attached to the end wall 18 and extends outwardly and generally perpendicular thereto. The shaft 24 includes one or more threads 26. The shaft 24 is adapted to removably attach the end cap 16 to the distal end of the handle 14. A generally conical spring 28 is located within the shaft 24 and is attached at one end to the interior surface of the end wall 18. The spring 28 is adapted to electrically engage a battery within the handle 14. The end wall 18 has a diameter which is approximately equal to the diameter of the handle 14.

A laryngoscope 40 including the lifting cap 42 of the present invention is shown in FIGS. 4 and 5. The lifting cap 42 is best shown in FIG. 3. The lifting cap 42 includes an abutment member such as a plate 44. The plate 44 includes a generally planar proximal surface 46 having an outer peripheral edge 48. The plate 44 also includes a generally planar distal surface 50 which is spaced apart from and generally parallel to the proximal surface 46. The distal surface 50 includes an outer peripheral edge 52. The plate 44 and its outer peripheral edges 48 and 52 are preferably circular, but can be formed in other configurations if desired. The plate 44 preferably has a diameter of approximately three inches, but may be formed in other diameters as desired so long as a sufficient area is provided for abutting engagement with the hand of a user which will prevent slipping of the user's hand along the handle of the laryngoscope 40.

The lifting cap 42 also includes a fastener such as an end cap 60 which may be formed substantially identical to the prior art end cap 16. The end cap 60 includes an end wall 61 that is attached to the proximal surface 46 of the plate 44. The end wall 61 of the end cap 60 is preferably attached to the proximal surface 46 by a weld which extends continuously around the circumference of the end wall 61. Alternatively, the end wall 61 of the end cap 60 can be attached to the plate 44 by an adhesive or by mechanical fasteners such as screws. The end cap 60 may also be integrally formed with the plate 44, or the end wall 61 can be replaced by the plate 44. The end cap 60 includes a generally tubular shaft 62 that extends outwardly from the end wall 61 and the proximal surface 46 and generally perpendicular to the end wall 61 and the proximal surface 46. If desired the shaft 62 can be attached directly to the proximal surface 46 of the plate 44. The shaft 62 includes one or more external threads 64. A generally conical spring 66 is located within the shaft 62 and is attached to the inner surface of the end wall 61 of the end cap 60.

The end cap 60 is attached to the proximal surface 46 of the plate 44 such that the shaft 62 is generally centrally located on the proximal surface 46. The end wall 61 has a diameter of approximately one and one-quarter (1-¼) inches. The proximal surface 46 of the plate 44 preferably extends approximately seven-eighths (⅞) of an inch from the end wall 61 of the end cap 60 to the outer peripheral edge 48 of the proximal surface 46. The plate 44 and end cap 60 are preferably made from metal, such as stainless steel, to facilitate sterilization.

As best shown in FIGS. 4 and 5, the laryngoscope 40 includes a blade 70 having a first end 72 and a second end 74. The first end 72 is adapted to be inserted into the oral opening of a patient. The laryngoscope 40 also includes a handle 76 having a first end 78 and a second end 80. The second end 80 of the handle 76 is coupled to the second end 74 of the blade 70. The handle 76 includes a central axis 82 which extends from the first end 78 to the second end 80. The handle 76 also includes a tubular shaft having an outer peripheral surface 84 which is generally cylindrical and which extends around the central axis 82. The peripheral surface 84 of the handle 76 has a diameter of approximately one and one-quarter (1-¼) inches.

As best shown in FIG. 4, the handle 76 includes a bore that is open at the first end 78 such that one or more batteries can be inserted into the handle 76 through the first end 78. The first end 78 of the handle 76 is internally threaded. The shaft 62 of the lifting cap 42 is adapted to threadably engage the first end 78 of the handle 76 such that the lifting cap 42 can be removably attached to the first end 78. The lifting cap 42 is rotated about the central axis 82 to insert the shaft 62 of the lifting cap 42 into the first end 78 of the handle 76 such that the shaft 62 is threadably connected to the first end 78.

When the lifting cap 42 is attached to the first end 78 of the handle 76, the plate 44 extends radially outwardly from adjacent the peripheral surface 84 of the handle 76 to the outer peripheral edge 48 of the proximal surface 46. The proximal surface 46 is located generally perpendicular to the handle 76 and central axis 82. The outer peripheral edge 48 of the proximal surface 46 is located outwardly from the peripheral surface 84 of the handle 76 a substantial distance such as approximately three-quarters (¾) of an inch or more. This enables a user to manually grasp the peripheral surface 84 of the handle 76 with their hand and to abut their hand against the proximal surface 46 of the lifting cap 42. The user can apply a lifting force to the laryngoscope 40 generally parallel to the central axis 82 of the handle 76 by pressing the user's hand against the proximal surface 46 of the lifting cap 42. The grip of the user on the handle 76 can be loosened as the plate 44 will prevent the user's hand from slipping along the peripheral surface 84 of the handle 76, while still allowing the user to control the orientation of the handle 76 during an endotracheal intubation procedure.

Use of a lifting cap 42 in connection with a laryngoscope reduces the amount of gripping pressure the user needs to apply to the handle of the laryngoscope, allows the user to apply a greater lifting force to the laryngoscope, promotes proper lifting direction of the laryngoscope, and reduces the number of attempts that may be required for a successful intubation. When desired, the lifting cap 42 can be removed from the handle 76 of the laryngoscope 40 and can be replaced with a standard end cap 16. The lifting cap 42 can be removed and replaced from the distal end of the handle 14 of a prior art laryngoscope 10.

Various features of the invention have been particularly shown and described in connection with the illustrated embodiment of the invention, however, it must be understood that these particular arrangements merely illustrate, and that the invention is to be given its fullest interpretation within the terms of the appended claims.

What is claimed is:

1. A laryngoscope for use in facilitating oral endotracheal intubation, said laryngoscope including:

a blade having a first end and a second end, said first end adapted to be inserted into a patient;

a handle adapted to be manually grasped by a hand of a user, said handle having a first end, a second end, a central axis extending from said first end to said second end of said handle, and a peripheral surface extending around said central axis, said second end of said handle being coupled to said blade; and a lifting cap including an abutment member adapted to be attached to said first end of said handle, said abutment member including a proximal surface that extends outwardly from adjacent said peripheral surface of said handle to an outer edge, said outer edge being located at least approximately three-quarters of an inch from said handle;

whereby the user can loosely grip said handle and the hand of the user can be pressed against said proximal surface of said lifting cap to move said handle in the proper direction to facilitate intubation while retaining control of the orientation of said handle.

2. The laryngoscope of claim 1 wherein said handle includes a generally tubular shaft.

3. The laryngoscope of claim 1 wherein said peripheral surface of said handle is generally cylindrical.

4. The laryngoscope of claim 1 wherein said proximal surface is generally planar.

5. The laryngoscope of claim 1 wherein said outer edge of said proximal surface extends around said central axis of said handle.

6. The laryngoscope of claim 1 wherein said first end of said handle is approximately centrally located with respect to said proximal surface of said abutment member.

7. The laryngoscope of claim 1 wherein said abutment member comprises a plate.

8. The laryngoscope of claim 7 wherein said plate includes a generally planar distal surface.

9. The laryngoscope of claim 1 wherein said outer edge of said abutment member is generally circular.

10. The laryngoscope of claim 1 including an end cap attached to said proximal surface of said abutment member, said end cap adapted to be attached to said first end of said handle.

11. The laryngoscope of claim 1 wherein said lifting cap includes a shaft extending outwardly from said proximal surface of said abutment member, said shaft adapted to be attached to said first end of said handle.

12. The laryngoscope of claim 11 wherein said shaft is generally cylindrical and includes at least one thread adapted to removably attach said lifting cap to said first end of said handle.

13. A lifting cap adapted to be attached to an end of a handle of a laryngoscope, said lifting cap including:

an abutment member having a proximal surface; and a fastener attached to said proximal surface of said abutment member, said proximal surface extending outwardly from said fastener to an outer edge spaced substantially apart from said fastener, said outer edge of said proximal surface being located at least approximately three-quarters of an inch from said fastener, said fastener adapted to attach said abutment member to the end of the handle of the laryngoscope.

14. The lifting cap of claim 13 wherein said fastener comprises an end cap.

15. The lifting cap of claim 14 wherein said end cap includes an end wall attached to said proximal surface and a threaded shaft extending outwardly from said end wall generally perpendicular to said proximal surface.

16. The lifting cap of claim 13 wherein said abutment member comprises a plate, said plate including said proximal surface.

17. The lifting cap of claim 13 wherein said proximal surface is generally planar.

18. The lifting plate of claim 13 wherein said outer edge of said proximal surface is generally circular.

* * * * *